United States Patent [19]

Trutnovsky et al.

[11] 3,953,296

[45] Apr. 27, 1976

[54] ENZYME RECOVERY BY ULTRAFILTRATION IN ENZYMATIC ANALYSIS

[75] Inventors: Helmut Trutnovsky, Graz-Andritz; Benno Paletta, Graz, both of Austria

[73] Assignee: The Kreidl Chemico Physical Kommanditgesellschaft, Schann

[22] Filed: July 24, 1974

[21] Appl. No.: 491,484

[30] Foreign Application Priority Data

July 26, 1973 Austria .............................. 6600/73
Feb. 11, 1974 Austria .............................. 1074/74

[52] U.S. Cl. ........................... 195/103.5 R; 195/127
[51] Int. Cl.² ....................... C12K 1/04; C12K 1/10
[58] Field of Search ............. 195/115, 139, 103.5 R, 195/127

[56] References Cited
UNITED STATES PATENTS 3,472,765   10/1969   Budd et al. .......................... 195/115
3,720,583   3/1973   Fisher ................................ 195/115

*Primary Examiner*—A. Louis Monacell
*Assistant Examiner*—C. A. Fan
*Attorney, Agent, or Firm*—Cushman, Darby & Cushman

[57] ABSTRACT

A method and device for producing low-molecular products, especially for determining the concentration of low-molecular biological substances, by means of enzyme reaction, characterized by the fact that, after the reaction is complete, the used enzyme is separated from the low-molecular substances of the reaction mixture by means of ultrafiltration, conducted into a circulation system, especially a continuous circulation system, and used again for enzymatic production of low-molecular substances.

7 Claims, 2 Drawing Figures

ENZYME RECOVERY BY ULTRAFILTRATION IN ENZYMATIC ANALYSIS

A chemical reaction catalyzed by specific enzymes is often used for producing low-molecular products of an enzyme reaction expecially for determining the concentration of biological substances. In that method, the test substance is mixed with suitable buffers and adjuvants, and the reaction that makes the quantitative determination possible is produced by the catalytic effect of the added enzyme. The determination is usual done by measuring the optic absorption. The enzymes necessary for this are available on the market, but are relatively expensive. In the processes known, the reaction mixture is discarded after the measurement, so that the expensive enzymes are lost. This invention therefore aims at avoiding this disadvantage and the method of the invention consists essentially of the fact that after the completed reaction, the used enzyme is separated from the low-molecular substance of the reaction mixture through ultrafiltration, led into circulation, especially continuous circulation, and used again for enzymatic production of low-molecular substances. This method makes full use of the fact that all enzymes differ so greatly in molecular weight from the adjuvants and test materials, that they can be separated from them by means of ultrafiltration. Thus the enzyme remains entirely in the concentrate, while the low-molecular components in the filtrate and concentrate are present in equal concentration. Since the amount of filtrate is significantly greater than the amount of concentrate, the ratio of enzymes to low-molecular substances in the concentrate is significantly greater than in the reaction mixture. On the basis of this fact, the re-use of the enzyme in the form of the concentrate is made possible.

After ultrafiltration, however, remains of the low-molecular components of the reaction mixture can still be found in the concentrate. According to the invention, the remains of dissolved low-molecular components of the reaction mixture left in the concentrate after reaction and ultrafiltration can be determined on the basis of the concentration measured after the reaction, and they can be considered in the calculation of the next determination, using the enzyme left in the concentrate. The amounts of low-molecular substances left in the concentrate can be determined from the determination of the concentration of low-molecular substances in a reaction. This is done by seeing to it that in the next reaction, which is performed with the enzymes left in the concentrate, the amounts of low-molecular substances left in the concentrate are considered in the calculations, whereby the result of the determination in the second reaction performed with the same enzyme fraction can be corrected to such an extent, that the measurement is exact again. In this way, the determination of concentration can be performed with the re-used enzyme in exactly the same manner as with a fresh enzyme. The calculation can be performed simply in an electronic computer, in which the data concerning the measurement performed previously with the same enzyme fraction are used. However, the calculation of the fraction of low-molecular substances left in the concentrated presupposes that a number of such determinations will be performed in direct sequence.

In accordance with a special mode of operation of the invention, the process can be performed in such a way that the concentrate flowing off the concentrate chamber of the ultrafilter can be ultrafiltered again after dilution, whereby this step can be repeated several times, and that the concentrate from the last ultrafiltration is again used for producing low-molecular products by means of enzyme reaction, especially for enzymatic determination of low-molecular biological substances. In the first ultrafiltration, the amount of low-molecular substances left in the concentrate is found from the ratio of concentrate to filtrate. If, for example, the proportion of concentrate to filtrate is 1:10, then only 1/10 of the low-molecular substances contained in the reaction mixture is left in the concentrate. If now the concentrate is diluted and ultrafiltered again, then it is found that in the case of the same proportion of concentrate to filtrate of 1:10, only 1/100 of the low-molecular substances contained in the reaction mixture are present in the concentrate. In many cases, such as fraction of low-molecular substances, which affects the results of the next determination, using the same enzyme, can be taken into account. The fraction of 1/100 low-molecular substances is in many cases already below margin of error for the determination, so that the enzyme can be re-used regardless of the accompanying low-molecular substances. In any case, however, this fraction is about equal again in the second and each subsequent instance of use of the enzyme, so that consideration of an always constant correction factor in the measurement is sufficient. However, if the concentrate is ultrafiltered again after dilution, then the amount of low-molecular substances in the concentrate is only 1/1000 of the amount contained, which is in nearly all cases lower than the margin of error for the determination.

Since in the case of repeated ultrafiltration, consideration of the fraction of low-molecular substances left in the concentrate is not necessary, it is also not necessary in these cases to take into account a result of the previous determination, and thus, in accordance with the invention, the concentrate of the last ultrafiltration can be stored before re-use. This is especially advantageous if a discontinuable process is used.

Measurement of the reaction mixture can be performed in the same way as was used in already known methods, when the reaction mixture was thrown away after measurement. According to the invention, however, the measurement is preferably taken on the filtrate flowing off the filtrate chamber of the first ultrafilter. This is easily possible, because the low-molecular substances are present in the filtrate in the same concentration as in the reaction mixture. This also offers the advantage that the measurement is not falsified by the high-molecular substances. The measurement is usually done with a photometer, which produces a heating of the material to be measured. The fact that measurement is performed on the filtrate offers the advantage that the enzymes are not harmed by the heat effect, which is of great significance, as these enzymes are to be re-used repeatedly. The method according to the invention is not limited to a determination of low-molecular biological substances by means of enzyme reaction but can also be used to produce low-molecular products by an enzyme reaction for other purposes.

In the device of the invention, for determining the concentration of low-molecular biological substances by means of enzyme reaction, the enzyme is mixed with the sample in the usual way at a mixing point, whereby the reaction mixture is conveyed by means of pump pressure through a reaction stretch, through a pipe, into a measuring point. In accordance with the invention, the pipe conducting the reaction mixture is connected to the entrance of the concentrate chamber of the ultrafilter, whereby the exit of the concentrate chamber is connected with the mixing point, and a discharge pipe is connected with the filtrate chamber. With such a device, it is possible to perform a great number of concentration determinations in uninterrupted succession, whereby however, if there is only one ultrafilter, an electronic computing and storing device is useful, for taking into account the fraction of low-molecular substances left in the concentrate and thus in the re-used enzyme solution, when viewing the previous determination performed with this enzyme fraction. According to a special mode of operation of the invention, therefore, the apparatus is arranged in such a way that the outlet of the concentrate chamber of the ultrafilter is connected with the inlet of the concentrate chamber of a second ultrafilter, and a pipe for the solution agent is connected with the inlet of the concentrate chamber of the second ultrafilter, and that the outlet of the concentrate chamber of this second ultrafilter is connected with the mixing point by means of a pipe, and that a discharge pipe is connected to the filtrate chamber of the second ultrafilter. In this case, the fraction of low-molecular substances left in the concentrate can generally be disregarded, so that an electronic computing and storing device is not necessary. When, in accordance with the invention, the pipe from the outlet of the concentrate chamber of the second ultrafilter leads to the mixing point through the concentrate chambers of other ultrafilters, to the inlets of which pipes for a solution agent are also connected, then the accuracy of the determination is even further increased.

The measuring point can be placed in front of the inlet of the concentrate chamber of the first ultrafilter; however, according to the invention the measuring point is placed within the discharge pipe leading out of the filtrate chamber of the first ultrafilter, whereby the advantages described above are achieved, in that the enzyme to be re-used is protected against heating and thus greatly spared.

When several ultrafilters are used, a storage container for the enzyme can be inserted into the pipe leading from the concentrate chamber of the last ultrafilter to the mixing point. In this tank, the enzyme or enzyme solution is stored before re-use.

In the drawing, the invention is diagrammatically explained, with reference to examples.

Figure 1:
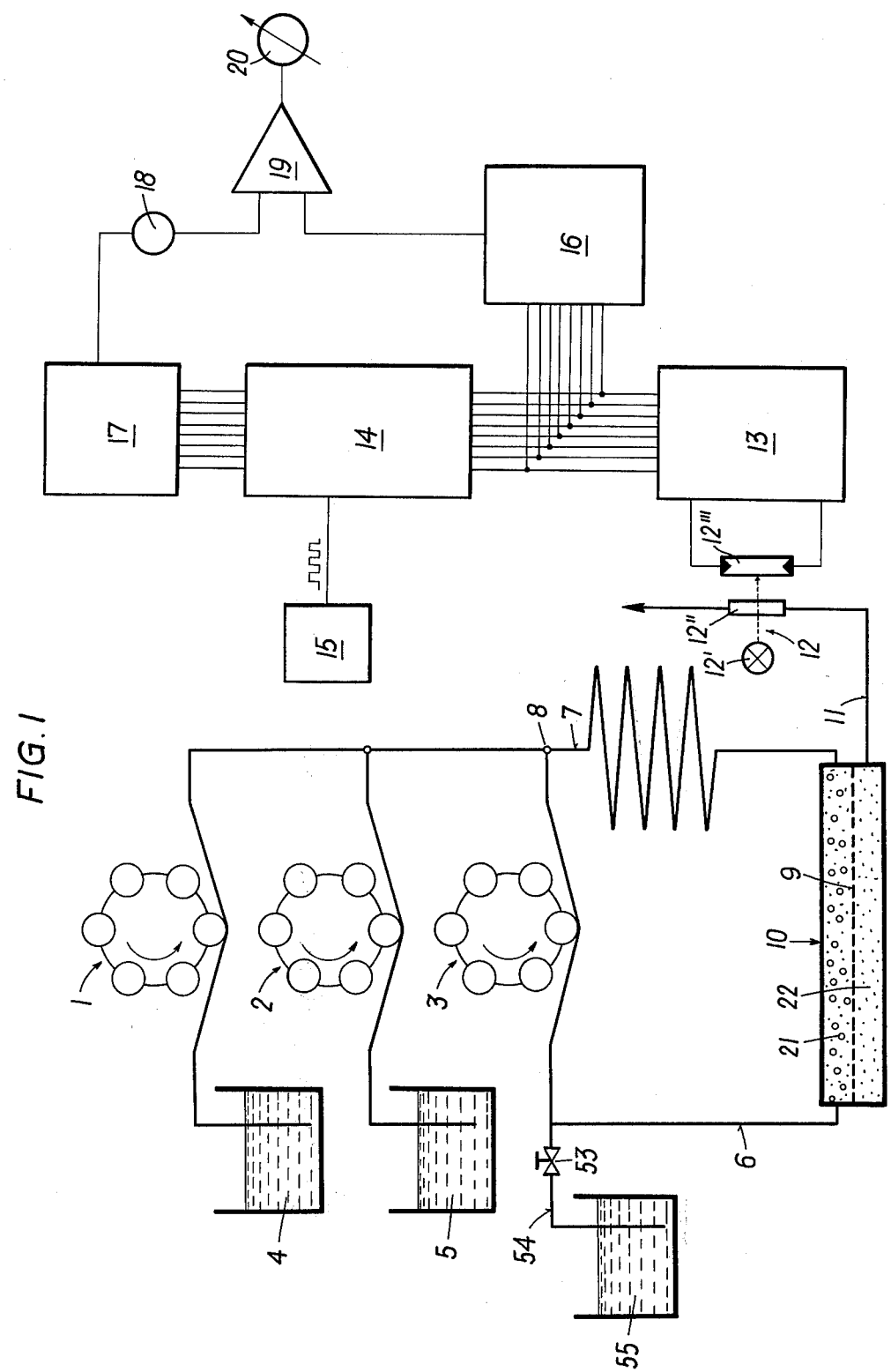
FIG. 1 shows a device for determining the concentration of low-molecular biological substances by means of enzyme reaction, using an ultrafilter.

In the case of the device represented in FIG. 1, there are three peristaltic pumps 1, 2 and 3. Peristaltic pump 1 draws in samples from the sample tank 4. The sample can be, for example, a solution containing glucose. Peristaltic pump 2 draws in an adjuvant for the glucose to be determined, e.g. a phosphate buffer containing o-anisidine as a chromogen, from the adjuvant tank 5. Peristaltic pump draws in enzyme solution, e.g. a solution of glucose-oxydase and a peroxydase, from the pipe 6, which is connected with a storage tank 55 for fresh enzyme solution through a valve 53 and a pipe 54. The solutions conveyed by the peristaltic pumps, operated, for example, by synchronous motors, are conducted to a mixing point 8, and the mixture thus obtained is conveyed through a pipe 7, in which the reaction takes place. This pipe can have, for example, an internal diameter of about 1 mm and be a polyethylene tube about 15 m long. The pipe with the reaction mixture 7 leads into the inlet of the concentrate chamber 21 of an ultrafilter 10 with a membrane 9. To the outlet of the concentrate chamber 21 of the ultrafilter 10 there is attached a pipe 6, through which the enzyme-rich concentrate is conducted back to the mixing point 8 with the help of a peristaltic pump 3. At this time, the valve 53 is closed, whereafter all subsequent determinations are performed on the concentrate of the ultrafiltration, and taking into account the measurements of previous determinations. The low-molecular substances freed by the enzyme and those dye-containing ones formed upon the enzymatic reaction, flow through a pipe 11 from the filtrate chamber 22 of the ultrafilter 10 to a photometer 12 (lamp 12', flow cell 12'' and photo resistance 12'''). The signal given off by the photo resistor 12''', which depends upon the concentration of dye in the solution flowing through the flow cell 12'', is registered in a logarithmic analog-digital-transformer and transformed into a digital signal that is registered in a slide register 14, in the present case a 16-stage register with 8 bits per stage.

The following should be considered in the analysis of the measurements given by the logarithmic analog-digital-transformer 13 and the measurements stored in digital form in the slide register 14.

In the case of the above-indicated diameter of the pipe 7, which is essentially identical to the pipe 11, the pipe system has a volume of about 15 to 20 ml between the peristaltic pumps 1, 2 and 3 on the one hand and the photometer 12 on the other, so that it is possible that a reacted and therefore colored solution could form in the photometer from the suctioned sample, still during suction of the substances from the sample container 4. If we assume that in the ultrafilter 10 the reaction mixture, in a volume ratio of 1:9, is separated into an enzyme concentrate flowing away through the pipe 6 and an ultrafiltrate flowing toward the photometer and containing the colored reaction product, and that the volume of the pipe 6 is so great that the enzyme solution used in the first test is re-used for the fourth test, then care must be taken that the values stored in the slide register 14 be stepped up by a timing generator 15 so fast, that the measurement entered into the slide register 14 for the first test should appear at the exit of this slide register 14 at the moment when the measurement for the fourth test is determined by the photometer 12. Since in the enzyme concentrate leaving the concentrate chamber 21 of the ultrafilter 10 and in the reacted solution leaving the filtrate chamber 22 of the ultrafilter 10 through the pipe 11 there is the same concentration of colored reaction product, the measurement appearing at the exit of the slide register 14 for the first test, with a volume ratio of 1:9, should be reduced, and the difference between the measurement for the fourth test and the reduced value for the first test should be indicated. Toward this end, the digital signal that appears as an initial value in the logarithmic analaog-digital-transformer 13 for the measurement of the fourth test, is transformed into an analog signal in a digital-analog-transformer 16, and the digital signal appearing simultaneously at the exit of the slide register 14 for the measurement of the first test is transformed into an analog signal in a digital-analog-transformer 17. This last analog signal is reduced in a reducer 18 according to the cited separation ratio of 1:9, whereupon the difference is obtained from the analog signal given by the digital-analog-transformer 16 and the signal given by the digital-analog-transformer 17 and reduced by the reducer 18. The difference is determined in a subtractor 19. This difference is indicated as an analog signal by means of a dial gauge 20, but can also be transformed into a digital representation by means of an analog-digital-transformer.

Since as a rule the analog signals given off by the photometer 12 for successive tests are of different values, there should be an appropriate lock, so that a new output variable does not appear in the output of the logarithmic analog-digital-transformer 13 until a constant absorbance value is indicated by the photometer 12 for a long period of time.

Since the test fluid, the solution of adjuvants and the enzyme solution are continuously being conveyed, it is simple to set up the device represented diagrammatically in FIG. 1. Only two periods need be measured empirically for this:

a. the period from drawing in of the sample to appearance of the colored, reacted solution in the photometer. This period remains the same when advancement of the material is constant, and should be taken into consideration in coordinating the measurements with the individual tests.

b. the period from the appearance of the colored, reacted solution to the reappearance of coloring of the solution flowing through the photometer due to a recirculated enzyme solution, in the case of constant advancement of the adjuvant solution and constant advancement of water by means of the peristaltic pump 1. The pulse frequency of the timing generator 15 should be set up in such a way that a determined measurement is advanced through all the levels of the slide register just after termination of this period.

Figure 2:
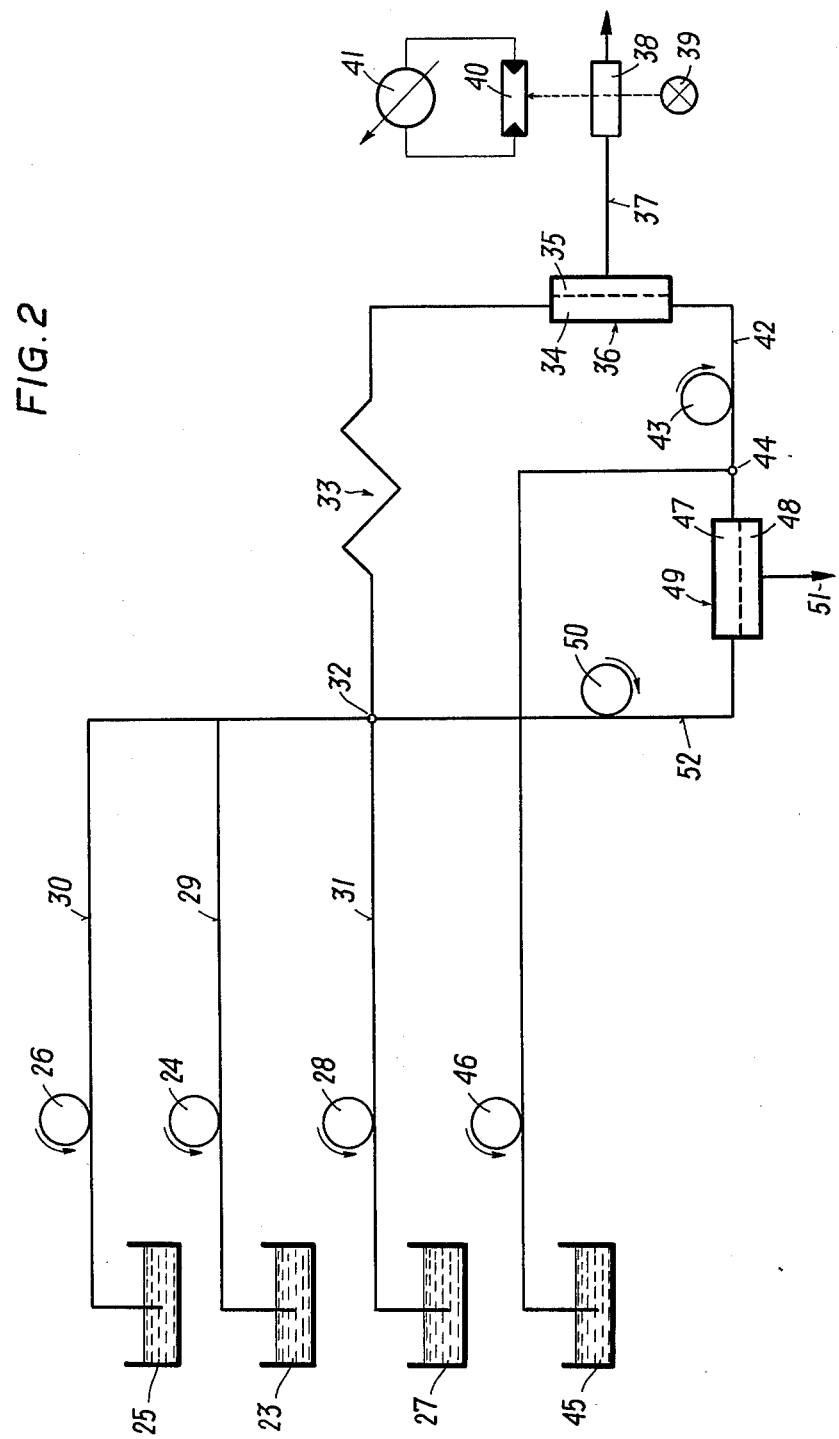
FIG. 2 shows this sort of device using several ultrafilters.

In FIG. 2, another device for performing the process of the invention is represented. A specimen is advanced from a container 23 by a peristaltic pump 24, an adjuvant solution is advanced from a container 25 by a peristaltic pump 26, and a first-filling enzyme is advanced from a container 27 by a peristaltic pump 28 through pipes 29, 30 and 31 to a mixing point 32. The reaction mixture is then conducted through a pipe 33, in which the reaction takes place, to the inlet of the concentrate chamber 34, of a first ultrafilter 36. Through a pipe 37, which is connected to the filtrate chamber 35 of the ultrafilter 36, the low-molecular components of the reaction mixture emerge and are conducted to the inlet of the flow cell 38 of a spectrophotometer. Here, the light emitted by a lamp 39 up to a certain wave length is filtered, and after passing through the flow cell 38 comes into contact with a photo resistor 40, whose resistance change is indicated by a measuring apparatus 41 either in the form of the light absorption or the extinction. The solution that issues from the flow cell 38 can be thrown away. A pipe 42 is connected with the outlet of the concentrate chamber 34 of the ultrafilter 36. The purified enzyme is suctioned through this pipe by a pump 43, and at 44 it is mixed with a diluting agent pumped out of a container 45 by a pump 46. The enzyme solution, which is now again diluted to about the original concentration, enters the concentrate chamber 47 of the ultrafilter 49 and is pumped from the outlet of this concentrate chamber 47 by a peristaltic pump 50 through a pipe 52 to the mixing point 32 and mixed with the specimen from the container 23. The introduction of the enzyme from the container 27 through the pipe 31 can be stopped by shutting down the pump 28 as soon as purified enzyme from the first test arrives at the mixing point 32 through the pipe 52. The low-molecular substances that emerge from the filtrate chamber 48 of the second ultrafilter 49 are conducted through a pipe 51 out of the filtrate chamber 48 and can be thrown away.

In this mode of operation of the device of the invention, purified enzyme is mixed with new test material at the mixing point 32, so that consideration of the low-molecular components left in the concentrate in calculations from previous determinations can be omitted in this case. FIG. 2 shows this mode of operation only diagrammatically, and it is equally self-evident that the test material from the test container 23 need not be the same in the case of several determinations in a series, and that a great number of similar containers 23 can be filled with different test specimens, the contents of which are advanced forward in a certain sequence by the pump 24, and the pipe 29 to the mixing point 32. Moreover, familiar devices can be provided for separating the individual test specimens, such as, for example, air bubble separators. More concentrate chambers and, if necessary, more places 44, in which diluting agents are mixed, can be added to the pipe 52, in addition to the concentrate chamber 47 of the second ultrafilter 49.

Examples

1. Determination of pyruvate with repeated use of lactate dehydrogenase

Pyruvate may be determined by its enzymatic reduction to lactate, noting that an equivalent amount of NADH will be oxidized to NAD. The change of the concentration in NADH will be photometrically measured at a wave length of 340 nm. The reaction takes place according to the equation

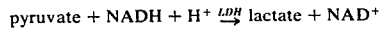

At a sufficient concentration of NADH (0.01 mMol) the chemical equilibrium is totally at the right hand side of the above equation.

The apparatus was assembled according to FIG. 2. As the pumps 24, 26 and 28, pumps of the type Ismatec mini were used together with a hose of a diameter of 0.8 mm and consisting of Tygon said pumps having a supply capacity of 0.75 ml per minute. The pump 46 used was equally a pump of the type Ismatec mini being equipped with a silicone hose of a diameter of 1.5 mm and having a supply capacity of 2.6 ml per minute. The pumps 43 and 50 were of the type LKB 4912A having a supply capacity of 0.2 ml per minute and being equipped with a silicone hose of a diameter of 1 mm. In a tangential stream housing having a diameter of 90 mm, filters of the type Amicon PM 30 were used (ultrafilters 36 and 49). The conduit 33 consisted of a polyethylene hose having a diameter of 1 mm and a length of 30 m and having a volume of 25 ml. All connecting conduits consisted of the same hose material.

The connecting components used were screwing fittings consisting of teflon and supplied by the firm Serva, Heidelberg. The conduit 33 was located within a ultrathermostat according to Hoeppler and kept at a temperature of 25°C. The total volume of the enzyme circuit was 37 ml including the filtrate portions. The photometer was of the type Zeiss PN2a with through-flow cuvette 38.

Reagents

By dissolving 46.6 g triethanolamine.HCl in 200 ml water and adding 0.94 g complexon III and further adjusting the pH to 7.6 by means of 2N—NaOH and adding water for a total volume of 250 ml a buffer solution having a pH of 7.6 was obtained. The solution of NADH was used in a 0.33 millimolar concentration within buffer solution. The LDH was used in form of a suspension of cristals as can be obtained on the market.

At the beginning of the determinations, the conduits 33, 42 and 52 were filled with LDH in buffer solution. For this purpose the cristal suspension containing 300 μg LDH was diluted with 31 ml buffer solution and the solution obtained was sucked instead of the sample. As soon as the enzyme circuit had been filled, a solution of NADH and, instead of the sample, water was supplied and the zero level was read from the photometer. Subsequently, the samples containing no proteins and maximally 0.1 μMol pyruvate per milliliter were sucked. By separating air bubbles, mixing of adjacent samples, which were supplied in time intervals of 60 seconds, was avoided. The extinction will decrease in proportion to the content in pyruvate according to the equation

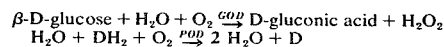

A calibrating curve is not necessary.

The enzyme solution remained fully active one week also with permanent use of the solution within the apparatus. With more extended working intervals it is to recommend to discharge the enzyme solution by opening a screwing connection and to store the solution at a temperature of 4°C.

2. Determination of D-glucose with repeated use of the glucose-oxydase and the peroxydase.

Glucose will be oxidized to gluconic acid and hydrogen peroxide by GOD in the presence of the oxygen of ambient air. The POD will transfer the oxygen of the $H_2O_2$ onto a chromogene and the extinction of the colouring matter formed will be determined. The reactions take place according to the equations:

$$\beta\text{-D-glucose} + H_2O + O_2 \xrightarrow{GOD} \text{D-gluconic acid} + H_2O_2$$
$$H_2O + DH_2 + O_2 \xrightarrow{POD} 2 H_2O + D$$

Both chemical equilibria are totally shifted to the right hand side of the above equations.

The apparatus used was assembled in an analogous manner to the apparatus described in (1). In particular the same pumps and the same connecting conduits were used. However, the ultrafilters 36 and 49 used were of the Amicon type PM 10. The ultrathermostat according to Hoeppler was adjusted to 35°C in this case. Reagents:

A buffer solution having a pH of 7 was prepared by dissolving 2.76 g $Na_2HPO_4 \cdot 2H_2O$ and 1.45 g $NaH_2PO_4 \cdot 2H_2O$ in 100 ml water. In this case, 100 mg ABTS (2,2'-azino-di-(3-ethylbenzthiazolon)-6-sulfonate) was used as the chromogene in 100 ml buffer solution. The glucose oxidase as well as the peroxidase were used in solid form (as can be obtained on the market), dissolved in buffer solution.

At the beginning of the determinations, the conduits 33, 42 and 52 were filled with GOD and POD in buffer solution. For this purpose 4 mg GOD and 1.5 mg POD were dissolved in 31 ml buffer solution and this solution was sucked instead of the sample, thereby sucking, instead of a solution of chromogene, pure buffer solution. As soon as the enzyme circuit had been filled, the solution of the chromogene was supplied and a calibrating curve was established by means of a plurality of standard solutions of glucose containing 1 to 20 μg glucose per milliliter. Subsequently the samples, which did not contain proteins and contained maximally 20 μg glucose per milliliter, were supplied. By separating air bubbles, intermixing of adjacent samples was avoided, the samples being supplied with a time interval of 60 seconds. The extinction is proportional to the content in glucose. Measurements were taken at a wave length of 420 nm and transformed by means of the calibrating curve into the sought results.

The enzyme solution remained fully active one week also with permanent use of the solution within the apparatus. During working intervals it is to recommend to discharge the enzyme solution by opening a screwing connection and to store the solution at a temperature of 4°C.

What we claim is:

1. In a method for determining the concentration of low-molecular biological substances by reaction with an enzyme including the steps of contacting a low molecular biological sample with an enzyme, thereby producing low molecular reaction products, quantitatively measuring the concentration of the low molecular reactions products and discarding the unreacted sample and the low molecular reaction products after measuring, the improvement of recovering a substantial portion of the enzyme comprising separating the low-molecular reaction products and unreacted sample from the enzyme by a first ultra-filtration into a filtrate containing substantially all of the low molecular reaction products and unreacted sample and a concentrate containing the enzyme and a trace quantity of the low molecular reaction products and unreacted sample, diluting the concentrate and subjecting the concentrate to at least one additional ultra-filtration, recovering the enzyme therefrom substantially devoid of low molecular reaction products and unreacted sample, and reusing the thus separated enzyme in the continuous concentration determination.

2. The method according to claim 1 wherein the recovered enzyme is stored prior to reuse.

3. The method according to claim 1 wherein the quantitative measurement of the concentration of the low molecular reaction products is effected on the filtrate separated from the first ultrafiltration step, and the concentration of the sample is calculated from the measured concentration of the low molecular reaction products.

4. An apparatus for quantitatively determining the concentration of low-molecular biological substances by reaction with an enzyme and production of low molecular reaction products including:
 a source of low-molecular biological sample;
 a source of reactive enzyme;
 pump means for delivering a predetermined quantity of sample from the sample source to a reaction area;
 pump means for delivering a predetermined quantity of reactive enzyme from the enzyme source to a reaction area;

means for mixing together the delivered sample and the delivered enzyme including therewith a reaction area;

pipe means communicating the reaction area to a first ultrafilter for separating a filtrate containing substantially all of the low molecular reaction products and unreacted sample from a concentrate containing the enzyme and a trace quantity of the same and low molecular reaction products;

a second ultra-filter for further concentrating the enzyme and removing trace portions of sample and low molecular reaction products therefrom;

pipe means communicating the concentrate of the first ultra-filter to a second ultra-filter;

a source of enzyme diluent intermediate the first and second ultra-filters for delivery of enzyme diluent to the concentrate passing from the first ultra-filter to the second ultra-filter;

pipe means communicated from the outlet of the second ultra-filter for delivering the separated, diluted enzyme substantially devoid of sample to the mixing means;

pipe means communicating the filtrate of the first ultra-filter to an outlet for discarding the unreacted low molecular sample and the low molecular reaction products, and means for determining the concentration of the low molecular reaction products for evaluation of the concentration of the low molecular biological sample.

5. The apparatus according to claim 4 further including:

a third ultra-filter for further concentrating the enzyme, said filter connected to the second ultra-filter via a communicating pipe therebetween for delivering filtered concentrate to the third ultra-filter;

a second source of enzyme diluent associated with the third ultra-filter intermediate the second and third ultra-filters for delivery of enzyme diluent to the concentrate passing from the second ultra-filter to the third ultra-filter; and pipe means communicated from only the outlet of the third ultra-filter for delivery of the diluted, separated enzyme substantially completely devoid of sample to the mixing means, the three ultra-filters connected in series.

6. The apparatus according to claim 5 further including:

storage means for the separated enzyme intermediate the pipe means from the third ultra-filter and the mixing means.

7. The apparatus according to claim 4 wherein the said means for determining the concentration of the low molecular reaction products is arranged in the said pipe means communicating the filtrate of the first ultra-filter to an outlet for discarding the unreacted low molecular sample and the low molecular reaction products.

* * * * *